United States Patent [19]
Vallejos et al.

[11] Patent Number: 6,057,474
[45] Date of Patent: May 2, 2000

[54] PREPARATION PROCESS FOR α, β-DICARBONYLATED COMPOUNDS

[75] Inventors: Jean-Claude Vallejos, Marseilles; Nicolas Capelle, Nimes; Henri Arzoumanian, Aubagne, all of France

[73] Assignee: Clariant S.A., Puteaux, France

[21] Appl. No.: 09/217,616

[22] Filed: Dec. 22, 1998

[30] Foreign Application Priority Data

Dec. 26, 1997 [FR] France ................ 97 16588

[51] Int. Cl.$^7$ .............. C07C 69/76; C07C 69/72; C07C 45/32; C07C 45/33
[52] U.S. Cl. .............. 560/51; 560/174; 568/312; 568/389
[58] Field of Search ............... 560/51, 54, 174; 568/312, 389

[56] References Cited

U.S. PATENT DOCUMENTS 5,523,459  6/1996  Hirai et al. .................. 560/51

OTHER PUBLICATIONS

J. Cossy et al., "Oxidative cleavage of 2–substituted cycloalkane–1, 3–diones and of cyclic beta–ketoesters by copper perchlorate/oxygen.", Tetrahedron Letters, vol. 35, No. 22, Aug. 15, 1994, pp. 6089–6092.

Ahmed Atlamsani et al., "Synthesis of 5–and 6–oxoalkanoic acids by copper(II)–catalized oxidative cleavage of cycloalkanones with dioxygen.", Synthesis, No. 1, Jan. 1993, pp. 79–81.

Zong–Xing Si et al., "A facile general route to alpha–keto esters and alpha–diketones.", Synthesis, No. 6, Jun. 1990, pp. 509–510.

Ito S. et al., "Ferric salt catalyzed oxydation of cycloalkanones to oxo esters by molecular oxygen.", Journal of Organic Chemistry, vol. 48, No. 7, Apr. 8, 1983, pp. 1133–1135.

*Primary Examiner*—Rosalynd Keys
*Attorney, Agent, or Firm*—Browdy and Neimark

[57] ABSTRACT

Preparation process for α,β-dicarbonylated compounds of formula (I)

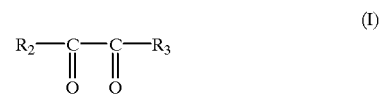

in which $R_2$=alkyl, phenyl or benzyl being able to be substituted in various ways on the cycle, or carboxylic ester, and $R_3$=alkyl or alkoxy or carboxylic ester in which a compound of formula (II)

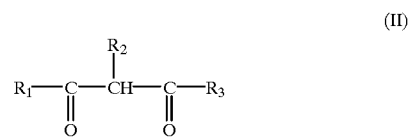

in which $R_1$=alkyl, or alkyl α-ketocarboxylate or carboxylic ester, and $R_2$ and $R_3$ have the same meanings as previously is reacted in a nitrile type solvent, with molecular oxygen in the presence of copper$^{II}$ nitrate or ferric chloride as catalyst, and use for obtaining ethyl α-ketobutyrate, ethyl phenyl pyruvate, ethyl pyruvate, ethyl phenylglyoxylate, butane-2, 3-dione or diethyl mesoxalate.

19 Claims, No Drawings

PREPARATION PROCESS FOR α, β-DICARBONYLATED COMPOUNDS

The present invention relates to a preparation process for α,β-dicarbonylated compounds.

In the literature, there are numerous synthetic routes for α-keto esters, α-keto acids and α,β-diketones.

For example, the following can be mentioned:

Kovacs, L. *Recd. Trav. Chim. Netherlands* 112, 471–496 (1996)

Cooper, A. J. L. et al, *Chem.Rev.* 83, 321–358 (1983),

Weinstock, L. M. et al, *Synth. Comm.* 11, 943 (1981),

Wislicenus *Ber*20., 592 (1887),

Friedman, L. and Kosower E. *Organic Syntheses*, Coll. Vol. III, 510,

Sohda, T. et al, *Chem. Pharm.* Bull. 30, 3601 (1982),

Inokushi, T. et al, *Chem. Lett.* 8, 1411–1414 (1994),

Muckawa, H. et al., *Chem. Lett.* 6, 1017–1020 (1994),

Bouveault, L. and Locquin R. *Bull. Soc. Chim.* Fr, 31, 1049, 1055, 1061, 1143(1904)

Locquin, R. *Bull Soc. Chim.* Fr. 31, 1068, 1147 (1904),

Si, Z et al, *Synthesis* 6, 509–510 (1990).

But none of the syntheses described allows an industrial use to be envisaged.

In fact, the processes described require either raw materials that are rarely available on the market, or expensive reagents, or operating conditions that cannot be recreated in an industrial environment, or are processes causing pollution.

Now, the Applicant was surprised to discover that it was possible to obtain α,β-dicarbonylated compounds economically and with good yields by reacting an appropriate starting compound with molecular oxygen in the presence of small quantities of an appropriate catalyst in an appropriate reaction solvent.

For this reason, a subject of the present Application is a preparation process for α,β-dicarbonylated compounds of formula (I)

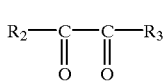
(I)

in which $R_2$ represents an alkyl radical containing 1 to 6 carbon atoms, or a phenyl radical or a benzyl radical, being able to be substituted in various ways on the cycle, in particular by alkyl substituents containing 1 to 6 carbon atoms, by alkoxy substituents containing 1 to 4 carbon atoms or by halogen substituents or a carboxylic ester radical containing 2 to 5 carbon atoms and $R_3$ represents an alkyl radical containing 1 to 4 carbon atoms, or an alkoxy radical containing 1 to 4 carbon atoms or a carboxylic ester radical containing 2 to 5 carbon atoms, characterized in that an α,γ dicarbonylated compound of formula (II)

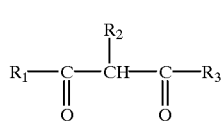
(II)

in which $R_1$ represents an alkyl radical containing 1 to 6 carbon atoms, or an alkyl α-keto carboxylate radical containing 3 to 6 carbon atoms or a carboxylic ester radical containing 2 to 5 carbon atoms and $R_2$ and $R_3$ have the same meanings as previously, is reacted in a nitrile type solvent with molecular oxygen in the presence of copper$^{II}$ nitrate or ferric chloride as catalyst.

The α,β-dicarbonylated compounds of formula I relate essentially to α-keto esters that provide access to α-keto acids and their derivatives which are very useful molecules both for use in biological systems and in organic synthesis. In fact, certain α-keto acids are used in the treatment of patients undergoing dialysis, this is the case, for example, for methylethyl pyruvic acid, dimethyl pyruvic acid or isopropyl pyruvic acid. Moreover, they are of great use as intermediates for numerous syntheses such as those for medicaments, inhibition enzymes, α-hydroxy acids, c-nucleosides, natural products, as well as for the synthesis of a large number of heterocycles.

They can also be α,β-diketones, very useful compounds for use in organic synthesis.

As an appropriate catalyst, it was discovered, surprisingly, that among the numerous salts of copper, iron, cobalt and manganese tested, only copper$^{II}$ nitrate and ferric chloride give useful synthesis yields which can be used industrially.

In addition, as an appropriate reaction solvent, it was discovered, surprisingly, that among the catalysts selected, only solvents of nitrile type, in particular aliphatic or aromatic, allowed synthesis yields to be obtained that are useful and can be used industrially, solvents of the aliphatic type giving the best yields.

The process according to the present invention allows α,β-dicarbonylated compounds of formula (I) above to be obtained economically and with good yields.

In formula I, in formula II and hereafter, the term alkyl radical containing 1 to 6 carbon atoms represents, for example, a methyl, ethyl, propyl, butyl, hexyl, cyclohexyl radical, preferably a methyl or ethyl radical, and in particular an ethyl radical.

In formula I and hereafter, the phenyl radical and benzyl radical can be substituted in various ways on the cycle by one or more substituents, preferably by 3 or 2 or 1 alkyl substituents containing 1 to 6 carbon atoms, alkoxy containing 1 to 4 carbon or halogen atoms, preferably chlorine or bromine and is preferably not substituted.

In formula I and hereafter, the term alkoxy radical containing 1 to 4 carbon atoms represents, for example, a butoxy or propyloxy or ethoxy or methoxy radical, preferably an ethoxy or methoxy radical and in particular an ethoxy radical.

In formula I, in formula II and hereafter, the term carboxylic ester radical containing 2 to 5 carbon atoms represents, for example, a butyl or propyl or ethyl or methyl carboxylate, preferably an ethyl or methyl carboxylate radical and in particular an ethyl carboxylate.

In formula II and hereafter, the term alkyl α-ketocarboxylate radical containing 3 to 6 carbon atoms represents, for example, a butyl, propyl, ethyl or methyl α-ketocarboxylate radical, preferably an ethyl or methyl α-keto carboxylate radical and in particular an ethyl α-ketocarboxylate radical.

Under preferred conditions for implementing the process of the invention, the nitrile-type reaction solvent will be of an aliphatic nitrile type, most particularly acetonitrile.

According to other preferred conditions for implementing the above process, the quantity of copper$^{II}$ nitrate or ferric chloride will be comprised between 0.1 molar equivalent and 0.001 molar equivalent and more particularly between 0.05 and 0.01 molar equivalent with respect to the starting substrate of formula (II).

According to other preferred conditions for implementing the above process, the reaction will be carried out in a medium saturated in oxygen, achieved by bubbling oxygen or air through the reaction medium.

According to other preferred conditions for implementing the above process, the reaction will be carried out in a medium saturated in oxygen, achieved under an oxygen pressure of 1 to 5 atmospheres.

Again under preferred conditions for implementing the above process, the oxygen used comes from an air supply or under an air pressure.

The process according to the invention will more particularly be implemented at ambient temperature but can be carried out at a higher temperature in order to reduce the reaction time or the quantity of catalyst used.

It should be further specified that the process according to the invention is enhanced by a greater dilution of the substrate in the nitrile-type solvent but that for an industrial use of the process, it is preferable to work at a concentration of the order of 20 to 25% by weight of the substrate in the nitrile-type solvent.

The process according to the invention is advantageously implemented by mixing in a receptacle such as a three-necked flask, 1 molar equivalent of the substrate of formula II, 0.05 to 0.01 molar equivalent of copper$^{II}$ nitrate or ferric chloride and 75 to 80% by weight of the nitrile-type solvent with respect to the weight of the substrate.

Preferably, the mixture is agitated whilst being maintained at the desired temperature, most often at ambient temperature, in particular while saturating the reaction atmosphere in oxygen by bubbling through or under a pressure of to 1 to 5 atmospheres.

The $\alpha,\beta$-dicarbonylated compound formed is then determined in the reaction medium. This product can be isolated and purified by methods known per se, and explained in the examples illustrating the present invention.

Among the $\alpha,\beta$-dicarbonylated compounds of formula I accessible by the process of the present invention, there can be mentioned:

ethyl $\alpha$-ketohexanoate ethyl $\alpha$-ketobutyrate ethyl phenylpyruvate ethyl pyruvate ethyl phenylglyoxylate butane-2,3-dione diethyl mesoxalate A subject of the present Application is also the use of the above process to obtain the above-mentioned $\alpha,\beta$-dicarbonylated compounds of formula (I) and in particular those above.

The following examples allow the present invention to be better understood.

EXAMPLE 1

In a 125 ml three-necked flask equipped with a thermometer, a magnetic stirrer, a tube supplying oxygen and a condenser surmounted by a gas washing bottle, the following are introduced:

24.7 g (0.13 mol., 1 eq.) of ethyl 2-n butylacetoacetate (purity 97%)

0.3204 g (1.3 mmoles, 0.01 eq.) of trihydrated copper$^{II}$ nitrate (purity 99% min)

and 100 g of acetonitrile.

The mixture is agitated under oxygen bubbling (100 ml/mn) whilst maintaining the temperature at 20–25° C. with a water bath.

The solvent and acetic acid formed are evaporated off under reduced pressure. Then, 100 ml of ethyl acetate and 30 ml of water are added. Agitation is carried out and the phases are separated. The organic phase is washed with 10 ml of water. Then the ethyl acetate is evaporated off under reduced pressure. The 23 g of crude product obtained are distilled. 17 g of ethyl $\alpha$-ketohexanoate (83% yield) is recovered which distills at 68° C./4 mmHg (lit. 84° C./10 mmHg).

(The structure of the product was confirmed by $H^1$ NMR analysis 200 MHz).

EXAMPLE 2

In a 100 ml three-necked flask equipped with a thermometer, a magnetic stirrer, a dipping tube supplying oxygen and a condenser surmounted by a gas washing bottle, the following are introduced:

0.98 g (6 mmoles) of ethyl 2-ethyl acetoacetate (purity ~97%), 0.0476 g (0.3 mmole, 0.05 eq.) of ferric chloride (purity ~98%), and 23.5 g of acetonitrile.

The mixture is agitated at 20° C. under oxygen bubbling (~30 ml/mn).

After reaction for 6 hours, 0.78 g of ethyl $\alpha$-ketobutyrate, i.e. a yield of 80% is determined in the medium by HPLC (by external calibration, after oximation with methoxylamine).

EXAMPLE 3

In a 500 ml three-necked flask equipped with a thermometer, a magnetic stirrer, a dipping tube, a condenser surmounted by a gas washing bottle, the following are introduced:

33 g of ethyl 2-benzylacetoacetate (purity 98% min) (0.147 moles), 1.80 g of trihydrated copper nitrate (purity 99% min) (7.45 mmoles), and 300 g of acetonitrile.

The reaction mixture is maintained for 6 hours at 20° C. under agitation and oxygen is bubbled through (60 ml/mn). 10 g of IRC 718 resin (Rohm and Haas) is added. The reaction mixture is maintained under agitation for 1 hour at ambient temperature, then the resin is filtered and washed on the filter with a little acetonitrile. The medium is concentrated at 40° C. with a rotary evaporator under reduced pressure provided by the water pump, then the crude product obtained is distilled. 2.5 g of benzaldehyde (boiling point= 55° C. under 2 mm of Hg) is recovered, then 7.5 g of a yellow oil which distills at 110–115° C. under 1 mm of Hg is recovered (lit. 149–151° C. under 15 mm of Hg) which is identified by NMR as being ethyl phenylpyruvate containing a small quantity of the enol form, structure confirmed by $H^1$ NMR200 Mz. The yield of ethyl phenylpyruvate is 27% with respect to the starting product.

EXAMPLE 4

In a 100 ml three-necked flask equipped with a thermometer, mechanical agitation, a condenser surmounted by a gas washing bottle, the following is introduced:

2.80 g of diethyl methylmalonate (purity 99%) (16 mmoles), 0.194 mg of trihydrated coppe/l nitrate (purity 99% min.) (0.8 mmole), and 32.2 g of acetonitrile.

The reaction mixture is maintained under agitation for 16 hours and oxygen is bubbled through (30 ml/mn). 1.74 g of ethyl pyruvate, i.e. a yield of 93.5% is determined by HPLC (by external calibration after oximation with methoxylamine).

EXAMPLE 5

In a 100 ml three-necked flask equipped with a thermometer, a magnetic stirrer, a dipping tube supplying oxygen and a condenser surmounted by a gas washing bottle, the following are introduced:

2.8 g (13 mmoles) of crude diethyl-2oxalylbutyrate (synthesized according to Organic Synthesis Coll. Vol. II, 272–273), 0.151 g (0.65 mmole) of trihydrated copper II nitrate (purity 99% min.), and 32.2 g of acetonitrile.

The reaction mixture is maintained under agitation and oxygen is bubbled for 16 hours at T=20° C. 1.44 g of ethyl α-ketobutyrate, i.e. a yield of 84.5% is determined in the reaction medium by HPLC (by external calibration after oximation with methoxylamine).

EXAMPLE 6

In a 500 ml three-necked flask equipped with a thermometer, mechanical agitation and a dipping tube for supplying oxygen, the following are introduced:

50 g of diethyl phenyl malonate (purity 98%) (0.207 mole), 2.55 g of copper$^{II}$ nitrate (purity 99% min) (10.5 mmoles), and 450 g of acetonitrile.

The reaction mixture is maintained under agitation and oxygen is bubbled through (60 ml/mn) for 12 hours at a temperature of 20° C. 20 g of the IRC 718 resin (Rohm and Haas) is added to the reaction medium and agitation is maintained for 1 hour at ambient temperature. The resin is filtered and washed with a small amount of acetonitrile. The filtrate is concentrated with a rotary evaporator under reduced pressure with a water pump, then distilled. The fraction which distills at 95–100° C. under 1 mm of Hg (lit. 80° C. under 0.2 mmHg) is recovered, i.e. 27.5 g corresponding to a yield of 74.6%.

The ethyl phenylglyoxylate structure was confirmed by $H^1$ NMR analysis 200 Mz.

EXAMPLE 7

In a 100 ml three-necked flask equipped with a thermometer, a magnetic stirrer, a gas supply and a condenser surmounted by a gas washing bottle, the following are introduced:

1.1571 g (9.7 mmoles) of 3-methylacetylacetone (technical)

0.1188 g (0.48 mmole) of trihydrated copper$^{II}$ nitrate (purity 99% min.), and 23.5 g of acetonitrile.

The temperature of the mixture is reduced to 5–10° C. with an ice bath. The reaction mixture is agitated under oxygen bubbling (30 ml/mn). 0.57 g of butan-2,3-dione (68% yield) is determined in the reaction medium by HPLC (by external calibration after oximation with methoxylamine) after 8 hours.

EXAMPLE 8

In a 100 ml three-necked flask equipped with a thermometer, a magnetic stirrer, a dipping tube supplying oxygen and a condenser surmounted by a gas washing bottle, the following are introduced:

0.656 g of diethyl 2-acetylmalonate techn. (3.24 mmoles), 0.0466 g of tridhydrated copper$^{II}$ nitrate (purity 99% min) (0.188 mmole), and 17 g of acetonitrile.

The reaction mixture is maintained under agitation and oxygen is bubbled through it (~30 ml/mn) at 20° C. for 16 hours. 1 g of IRC 718 resin (Rohm and Haas) is added. The reaction mixture is maintained under agitation for 1 hour at ambient temperature. The resin is filtered and washed with a small amount of acetonitrile. In the filtrate (18.7 g), 0.20 g of diethyl mesoxalate, i.e. a yield of 32.5% is determined by capilliary GC (internal calibration, diethyl oxalate standard).

COMPARISON EXAMPLE 1

In a 100 ml three-necked flask equipped with a thermometer, a magnetic stirrer, a dipping tube supplying oxygen and a condenser surmounted by a gas washing bottle, the following are introduced:

0.98 g (6 mmoles) of ethyl 2-ethylacetoacetate (purity ~97%), catalyst at the rate of 0.05 eq., and 23.5 g of acetonitrile.

The mixture is agitated at 20° C. under oxygen bubbling (~30 ml/mn).

After reaction for 2 to 4 hours, the ethyl α-ketobutyrate formed is determined in the medium by HPLC (external calibration after oximation with methoxylamine).

The results are recorded in the following Table 1:

TABLE I

| | | | Yield (%) * | |
|---|---|---|---|---|
| Test | Catalysts | Solubility | 2 hrs | 4 hrs |
| 1 | $Cu(NO_3)_2, 3H_2O$ | soluble | 75 | >95 |
| 2 | $Cu(ClO_4)_2, 6H_2O$ | soluble | 8 | 27 |
| 3 | $Cu(OAc)_2 4H_2O$ | soluble | 3 | 4 |
| 4 | $CuCl_2, 2H_2O$ | soluble | 3 | 7 |
| 5 | $CuCl_2$ | soluble | 2 | 5 |
| 6 | $Cu(SO_4)_2, 5H_2O$ | slightly soluble | 3 | 4 |
| 7 | $CuBr_2$ | soluble | 0 | 0 |
| 8 | CuCl | soluble | 0 | 4 |
| 9 | $CuCO_2, Cu(OH)_2$ | slightly soluble | 0 | 0 |
| 10 | Cu acetylacetonate | slightly soluble | 0 | 0 |
| 11 | Cu ethylacetoacetate | slightly soluble | 0 | 0 |
| 12 | $FeCl_3$ | soluble | 65 | 85 |
| 13 | $Fe(NO_3)_3, 9H_2O$ | soluble | 24 | 27 |
| 14 | $Co(OAc)_2, 4H_2O$ | slightly soluble | 1 | 4 |
| 15 | $CoCl_2, 6H_2O$ | soluble | 7 | 13 |
| 16 | $Co(NO_3)_2, 6H_2O$ | soluble | 0 | 0 |
| 17 | $Co(SO_4)_2, 7H_2O$ | slightly soluble | 0 | 0 |
| 18 | $Mn(OAc)_2, H_2O$ | slightly soluble | 4 | 9 |
| 19 | $MnCl_2, 4H_2O$ | slightly soluble | 2 | 3 |
| 20 | $Mn(NO_3)_2, 6H_2O$ | soluble | 0 | 0 |

* determined by HPLC dosage in the reaction medium (by external calibration after oximation with methoxylamine)

Analysis of these results clearly shows that the Cu$^{II}$ nitrate (test 1) and the ferric chloride (test 12) are by far the most effective catalysts compared with all other catalysts tested.

COMPARISON EXAMPLE 2

In a 100 ml three-necked flask equipped with a thermometer, a magnetic stirrer, a gas supply and a condenser surmounted by a gas washing bottle, the following is weighed:

0.98 g (6 mmoles, 1 eq) of ethyl 2-ethylacetoacetate (purity ~97%) 0.0732 g (0.3 mmole 0.05 eq.) of trihydrated copper$^{II}$ nitrate (purity 99% min) is added dissolved in various nitrile-type solvents (concentration by mass of substrate: 4% with respect to the solvent).

The mixture is agitated whilst maintaining the temperature at 20° C. with a water bath under oxygen bubbling (30 ml/mn). The ethyl α-ketobutyrate formed is determined in the reaction medium as a function of the reaction time by HPLC (by external calibration after oximation with methoxylamine).

The results are recorded in the following Table II:

TABLE II

| Test | 21 | 22 | 23 | 24 | 25 | 26 |
|---|---|---|---|---|---|---|
| Nitriles | MeCN | EtCN | ~~~CN | >-CN | >+CN | Ar-CN |
| Yield (%) * at | | | | | | |
| 2 hrs | 75 | 70 | 60 | 75 | 75 | 10 |
| 4 hrs | >95 | 95 | 90 | 85 | 85 | 25 |
| 6 hrs | >95 | >95 | >95 | 95 | 95 | 62 |
| 8 hrs | >95 | >95 | >95 | >95 | >95 | 70 |

*determined by HPLC dosage in the reaction medium (by external calibration after oximation with methoxylamine)

The Cu$^{II}$ nitrate possesses approximately the same reactivity in the different aliphatic nitriles. It is slightly lower in the aromatic nitrites.

COMPARISON EXAMPLE 3

The effectiveness of the catalysts Cu(NO$_3$)$_2$, 3H$_2$O and FeCl$_3$ in various polar, apolar, protic, aprotic solvents and in solvent mixtures, was studied.

In a 100 ml three-necked flask equipped with a thermometer, a magnetic stirrer, a dipping tube, the following were introduced:

0.98 g (6 mmoles) of ethyl 2-ethylacetoacetate (purity ~97%),

Cu(NO$_3$)$_2$, 3H$_2$O or FeCl$_3$ catalyst at the rate of 0.05 eq. and various solvents or solvent mixtures.

The mixture is agitated at 20° C. under oxygen bubbling (~30 ml/mn).

After reaction for 2 to 4 hours, the ethyl a-ketobutyrate formed is determined in the medium by HPLC (by external calibration after oximation with methoxylamine).

The results are recorded in the following Table III:

TABLE III

| | | | Yield (%)* | |
|---|---|---|---|---|
| Test | Catalysts | Solvent | 2 hrs | 4 hrs |
| 21 | Cu(NO$_3$)$_2$, 3H$_2$O | acetonitrile | 75 | >95 |
| 27 | Cu(NO$_3$)$_2$, 3H$_2$O | acetic acid | 0 | 0 |
| 28 | Cu(NO$_3$)$_2$, 3H$_2$O | ethanol | 0 | 0 |
| 29 | Cu(NO$_3$)$_2$, 3H$_2$O | ethyl acetate | 0 | 0 |
| 30 | Cu(NO$_3$)$_2$, 3H$_2$O | dimethylformamide | 0 | 0 |
| 31 | Cu(NO$_3$)$_2$, 3H$_2$O | toluene | 0 | 0 |
| 32 | FeCl$_3$ | acetonitrile | 65 | 85 |
| 33 | FeCl$_3$ | acetic acid | 0 | 0 |
| 34 | FeCl$_3$ | ethanol | 0 | 0 |
| 35 | FeCl$_3$ | ethyl acetate | 0 | 0 |
| 36 | Cu(NO$_3$)$_2$, 3H$_2$O | MeCN/water (75-25) | 0 | 0 |
| 37 | Cu(NO$_3$)$_2$, 3H$_2$O | MeCN/water (95-5) | 19 | 33 |
| 38 | Cu(NO$_3$)$_2$, 3H$_2$O | MeCN/toluene (30-70) | 35 | 47 |

TABLE III-continued

| | | | Yield (%)* | |
|---|---|---|---|---|
| Test | Catalysts | Solvent | 2 hrs | 4 hrs |
| 39 | Cu(NO$_3$)$_2$, 3H$_2$O | MeCN/toluene (5-95) | 0 | 0 |
| 40 | Cu(NO$_3$)$_2$, 3H$_2$O | MeCN/MeCOOEt (5-95) | 0 | 0 |
| 41 | Cu(NO$_3$)$_2$, 3H$_2$O | MeCN/MeCOOEt (10-90) | 15 | 28 |
| 42 | Cu(NO$_3$)$_2$, 3H$_2$O | MeCN/MeCOOEt (20-80) | 45 | 65 |

*determined by HPLC dosage in the reaction medium (by external calibration after oximation with methoxylamine)

The copper$^{II}$ nitrate and the ferric chloride only show any catalytic activity in acetonitrile. They have no activity in the other solvents, in particular in acetic acid and ethanol.

These results also show that the reaction can be carried out in solvent mixtures. However, the presence of acetonitrile is essential, and the speed of the reaction increases when the proportion of acetonitrile increases.

EXAMPLE 9

The effectiveness of the quantity of the catalyst Cu(NO$_3$)$_2$, 3H$_2$O on the speed of the reaction was also studied.

In a 100 ml three-necked flask equipped with a thermometer, a magnetic stirrer, a dipping tube supplying oxygen and a condenser surmounted by a gas washing bottle, the following were introduced:

0.98 g (6 mmoles) of ethyl 2-ethylacetoacetate (purity ~97%),

Cu(NO$_3$)$_2$, 3H$_2$O catalyst at the rate of 0.05 to 0.001 eq., and 23.5 g of acetonitrile.

The mixture is agitated at 20° C. under oxygen bubbling (~30 ml/mn).

After reaction for 2 to 4 hours, the ethyl α-ketobutyrate formed is determined in the medium by HPLC (by external calibration after oximation with methoxylamine).

The results were recorded in the following Table IV:

TABLE IV

| Test | Concentration by mass of β-keto ester (%) | Quantity of catalyst (molar %) | Reaction temperature | Yield (%)* | | | |
|---|---|---|---|---|---|---|---|
| | | | | 2 hrs | 4 hrs | 6 hrs | 8 hrs |
| 43 | 4 | 5 | ambient | 75 | >95 | >95 | >95 |
| 44 | 8 | 5 | ambient | 90 | >95 | >95 | >95 |
| 45 | 4 | 1 | ambient | 31 | 71 | 95 | >95 |
| 46 | 12 | 1 | ambient | 71 | 81 | 91 | >95 |
| 47 | 20 | 1 | ambient | 41 | 82 | 95 | >95 |
| 48 | 30 | 1 | ambient | 46 | 57 | 66 | 73 |
| 49 | 90 | 2 | ambient | 17 | 21 | 34 | 48 |
| 50 | 20 | 0.1 | 50° C. | / | / | >95 | >95 |

*determined by HPLC dosage in the reaction medium (by external calibration, after oximation with methoxylamine).

The reaction is enhanced by increasing the quantity of metallic salt. A higher temperature allows this quantity to be reduced. The quantity of nitrile is equally significant. A concentration of 20 to 25% of substrate in the mixture is preferred.

EXAMPLE 10

In a 100 ml three-necked flask equipped with a thermometer, a magnetic stirrer, a gas supply and a condenser surmounted by a gas washing bottle, the following are introduced:

0.98 g (6 mmoles, 1 eq.) of ethyl 2-ethylacetoacetate (purity ~97%)

0.0732 g (0.3 mmole 0.05 eq.) of trihydrated copper$^{II}$ nitrate (purity 99% min), and 23.5 g of acetonitrile.

The mixture is agitated whilst maintaining the temperature at 20° C. with a water bath under air bubbling (85 ml/mn). 0.78 g of ethyl α-ketobutyrate is determined in the reaction medium after 4 hours by HPLC (by external calibration after oximation with methyloxylamine) (yield >95%).

EXAMPLE 11

In a 2 l glass autoclave equipped with mechanical agitation, a gas supply, a thermometer and a double jacket oil circulation heater, the following are introduced:

135 g (0.85 mol, 1 eq.) of ethyl 2-ethylacetoacetate 2 g (0.0085 mol, 0.01 eq.) of trihydrated copper$^{II}$ nitrate, 500 g of acetonitrile.

The mixture is agitated whilst maintaining the temperature constantly below 40° C. and the reactor is charged with oxygen under a pressure of 5 bars. As soon as the pressure drops below 2 bars, the oxygen is recharged (5 bars), and so on until the oxygen consumption is negligible (approximately 6 hours).

The medium is then distilled under reduced pressure and 77 g of ethyl α-ketobutyrate is obtained, i.e. a yield of approximately 70% (by direct GC).

We claim:

1. Preparation process for α,β-dicarbonylated compounds of formula (I)

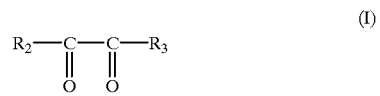

in which R$_2$ represents an alkyl radical containing 1 to 6 carbon atoms, or a phenyl radical or a benzyl radical being able to be substituted in various ways on the cycle, or a carboxylic ester radical containing 2 to 5 carbon atoms, and R$_3$ represents an alkyl radical containing 1 to 4 carbon atoms, or an alkoxy radical containing 1 to 4 carbon atoms, or a carboxylic ester radical containing 2 to 5 carbon atoms characterized in that an α,γ dicarbonylated compound of formula (II)

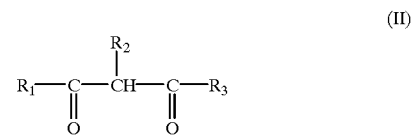

in which R$_1$ represents an alkyl radical containing 1 to 6 carbon atoms, or an alkyl α-ketocarboxylate radical containing 3 to 6 carbon atoms or a carboxylic ester radical containing 2 to 5 carbon atoms, and R$_2$ and R$_3$ have the same meanings as previously is reacted in a nitrile solvent, with molecular oxygen in the presence of copper$^{II}$ nitrate or ferric chloride as catalyst.

2. Process according to claim 1, characterized in that the reaction solvent is an aliphatic or aromatic nitrile solvent.

3. Process according to claim 2, characterized in that the reaction solvent is of an aliphatic nitrile.

4. Process according to claim 3, characterized in that the quantity of copper$^{II}$ nitrate or ferric chloride is comprised between 0.1 molar equivalent and 0.001 molar equivalent with respect to the starting substrate of formula (II).

5. Process according to claim 4, characterized in that the quantity of copper$^{II}$ nitrate or ferric chloride is comprised between 0.05 molar equivalent and 0.01 molar equivalent with respect to the starting substrate of general formula (II).

6. Process according to claim 5, characterized in that the reaction is carried out in a medium saturated in oxygen achieved by bubbling oxygen or air through the reaction mixture.

7. Process according to claim 5, characterized in that the reaction is carried out in a medium saturated in oxygen achieved under an oxygen pressure of 1 to 5 atmospheres.

8. Process according to claim 7, characterized in that the oxygen used comes from an air supply or under an air pressure.

9. Process according to claim 6, characterized in that the oxygen used comes from an air supply or under an air pressure.

10. Process according to claim 1, characterized in that the quantity of copper$^{II}$ nitrate or ferric chloride is comprised between 0.1 molar equivalent and 0.001 molar equivalent with respect to the starting substrate of formula (II).

11. Process according to claim 10, characterized in that the quantity of copper$^{II}$ nitrate or ferric chloride is comprised between 0.05 molar equivalent and 0.01 molar equivalent with respect to the starting substrate of general formula (II).

12. Process according to claim 1, characterized in that the reaction is carried out in a medium saturated in oxygen achieved by bubbling oxygen or air through the reaction mixture.

13. Process according to claim 1, characterized in that the reaction is carried out in a medium saturated in oxygen achieved under an oxygen pressure of 1 to 5 atmospheres.

14. Process according to claim 3, characterized in that the reaction is carried out in a medium saturated in oxygen achieved by bubbling oxygen or air through the reaction mixture.

15. Process according to claim 3, characterized in that the reaction is carried out in a medium saturated in oxygen achieved under an oxygen pressure of 1 to 5 atmospheres.

16. In a method of making a compound of ethyl α-ketobutyrate, ethyl phenylpyruvate, ethyl pyruvate, ethyl phenylglyoxylate, butane-2, 3-dione or diethyl mesoxalate comprising carrying out the process of claim 1 and recovering said compound.

17. In a method of making a compound of ethyl α-ketobutyrate, ethyl phenylpyruvate, ethyl pyruvate, ethyl phenylglyoxylate, butane-2, 3-dione or diethyl mesoxalate comprising carrying out the process of claim 2 and recovering said compound.

18. In a method of making a compound of ethyl α-ketobutyrate, ethyl phenylpyruvate, ethyl pyruvate, ethyl phenylglyoxylate, butane-2, 3-dione or diethyl mesoxalate comprising carrying out the process of claim 3 and recovering said compound.

19. In a method of making a compound of ethyl α-ketobutyrate, ethyl phenylpyruvate, ethyl pyruvate, ethyl phenylglyoxylate, butane-2, 3-dione or diethyl mesoxalate comprising carrying out the process of claim 4 and recovering said compound.

* * * * *